(12) United States Patent
Hansen (10) Patent No.: US 8,500,741 B2
(45) Date of Patent: Aug. 6, 2013

(54) PEDICLE SCREW EXTENSION ALIGNMENT

(76) Inventor: Stephen M. Hansen, St. George, UT (US)

( * ) Notice: Subject to any disclaimer, the term of this patent is extended or adjusted under 35 U.S.C. 154(b) by 39 days.

(21) Appl. No.: 12/875,057

(22) Filed: Sep. 2, 2010

(65) Prior Publication Data

US 2012/0059420 A1 Mar. 8, 2012

(51) Int. Cl.
*A61B 17/70* (2006.01)
(52) U.S. Cl.
USPC .......... 606/86 A; 606/914; 606/103; 606/104; 606/105
(58) Field of Classification Search
USPC ........ 606/914–916, 86 A, 103, 104, 250–279
See application file for complete search history.

(56) References Cited

U.S. PATENT DOCUMENTS

| | | | | |
|---|---|---|---|---|
| 4,479,661 A * | 10/1984 | Weigl | | 280/279 |
| 6,235,028 B1 | 5/2001 | Brumfield et al. | | |
| 7,179,261 B2 * | 2/2007 | Sicvol et al. | | 606/86 A |
| 7,527,638 B2 | 5/2009 | Anderson et al. | | |
| 2005/0065517 A1 | 3/2005 | Chin | | |
| 2006/0264934 A1 | 11/2006 | Fallin | | |
| 2007/0093824 A1 | 4/2007 | Hestad et al. | | |
| 2007/0173831 A1 * | 7/2007 | Abdou | | 606/61 |
| 2007/0213716 A1 * | 9/2007 | Lenke et al. | | 606/61 |
| 2008/0114403 A1 | 5/2008 | Kuester et al. | | |
| 2008/0125817 A1 | 5/2008 | Arnett et al. | | |
| 2008/0140120 A1 | 6/2008 | Hestad et al. | | |
| 2008/0312703 A1 | 12/2008 | Hestad et al. | | |
| 2009/0099605 A1 * | 4/2009 | Fallin et al. | | 606/252 |
| 2009/0326586 A1 * | 12/2009 | Duarte | | 606/264 |
| 2011/0077689 A1 * | 3/2011 | Mickiewicz et al. | | 606/277 |
| 2011/0172714 A1 * | 7/2011 | Boachie-Adjei et al. | | 606/264 |
| 2011/0196426 A1 * | 8/2011 | Peukert et al. | | 606/279 |

* cited by examiner

*Primary Examiner* — Jan Christopher Merene
(74) *Attorney, Agent, or Firm* — Thorpe North & Western LLP (57) ABSTRACT

Alignment clamps, extension caps, and systems, with associated methods, for pedicle screw extension alignment in an orthopedic patient are described. An alignment clamp for alignment of pedicle screw extensions includes a clamp having a hollow interior. The clamp can receive a pedicle screw extension through the hollow interior. The clamp includes opposing open ends in communication with the hollow interior. A straightening rod receptacle is on a side of the clamp. The straightening rod receptacle is oriented to receive a straightening rod therethrough. The straightening rod receptacle can be substantially perpendicular to a direction of the clamp through which the pedicle screw extension is receivable.

13 Claims, 10 Drawing Sheets

PEDICLE SCREW EXTENSION ALIGNMENT

BACKGROUND

In human anatomy, the vertebral column (i.e., backbone or spine) is a column typically consisting of bones and tissue, including 33 vertebrae, situated in the dorsal area of the torso. The vertebral column serves to house and protect the spinal cord in a spinal canal.

Occasionally, abnormalities, disease, trauma, and so forth can cause a spinal column disorder. One type of spinal disorder includes spinal deformity. Deformities include spondylolilsthesis, retrolisthesis, kyphosis, and scoliosis. Spondylolisthesis is an anterior or forward slip of one vertebra on another. In contrast, retrolisthesis is a posterior displacement of one vertebral body with respect to the adjacent vertebral segment. Kyphosis is an exaggerated kyphotic (posterior) curvature in the thoracic region that produces a "hump back", a condition commonly observed in osteoporosis. Scoliosis is a rotational deformity of the spine, and in adults, may include a lateral displacement as well known as lateral olisthesis. Scoliosis the most common abnormal curvature, occurring in 0.5% of the population. It is subdivided into degenerative scoliosis, which affects adults, and various forms of pediatric scoliosis, the most common of which is adolescent idiopathic scoliosis.

Spinal column disorders can result in significant pain as well as diminished nerve function. Some spinal column disorders are addressed using a spinal fixation technique. In spinal fixation, implants are used for fusing or immobilizing adjacent vertebrae. Spinal fixation can improve the position of the adjacent vertebrae relative to one another and can alter the overall alignment and/or curvature of the spine. Spinal fixation or instrumentation can immobilize the spine internally in order to promote fusion between vertebrae. Fusion is a process which can take up to several months or a year.

One spinal fixation technique includes using orthopedic contouring rods which run generally parallel to the spine. This technique often involves an invasive surgical procedure to expose the spine and attach pedicle screws to the pedicles of the appropriate vertebrae. The pedicle screws are configured to receive the orthopedic contouring rod which can be bent to achieve the desired curvature of the spinal column.

Traditionally, pedicle screws have been inserted through one major central incision, where muscles and other tissues are dissected off of the spine and retracted to the side to facilitate visualization of the deep spinal bones. Under direct visualization, with or without radiological imaging, pedicle screws are placed into the pedicles of the vertebral bodies, and then rods are typically placed to connect pedicle screws from one bone to those of other bones through the tulip. Since there are two pedicles for each vertebral body, one on the right and one on the left, a construct will most typically have two rods, one which connects pedicle screws on the right side, and another that connects pedicle screws on the left side. When the screws and rods are placed through this central incision, surgeons visualize the anatomy well, but at the cost of significant stripping of the muscle tissue which then is scarred, often devascularized, and potentially a source of pain in the future for the patients. Hence, the large, open exposure causes some disability or harm to the patient.

In contrast, if pedicle screws are placed through tiny incisions with reliance on radiographic visualization, not direct visualization, surgeons can instrument the spine with minimal muscle and tissue destruction. In other words, percutaneously placed pedicle screws can potentially save the patient the significant trauma caused by the traditional open exposure of the spine through the central incision. Unfortunately, in long constructs where several pedicle screws are inserted through percutaneous techniques, contouring a rod that will fit into the patient's anatomy can be difficult since a trial malleable rod cannot be trialed into the tulips under direct visualization. Typically with long constructs done percutaneously, contouring the rod can take significant amounts of time, as the rod often is passed through a small incision a the top of the construct, removed, contoured differently, passed again, and recontoured until the rod is fully contoured. The process of contouring the rod takes significant amount of time that, if diminished, could lead to shorter patient operative time, less anesthesia, less blood loss, less risk for complications, and better patient outcomes.

Improper alignment and inaccurate bending of the contouring rod decreases the effectiveness of the spinal fixation and can increase surgical difficulty and time expenditure. In combination with the incisions involved in for the installation of the contouring rod, extended surgical procedures and related difficulties or complications are generally recognized as major contributing influences for extended patient recovery and sub-optimal spinal fixation results.

SUMMARY

Alignment clamps, extension caps, and systems, with associated methods, for pedicle screw extension alignment in an orthopedic patient are described.

An alignment clamp for alignment of pedicle screw extensions includes a clamp having a hollow interior. The clamp can receive a pedicle screw extension through the hollow interior. The clamp includes opposing open ends in communication with the hollow interior. A straightening rod receptacle is on a side of the clamp. The straightening rod receptacle is oriented to receive a straightening rod therethrough. The straightening rod receptacle can be substantially perpendicular to a direction of the clamp through which the pedicle screw extension is receivable.

An extension cap for a pedicle screw extension includes an extension cap body. A hollow interior can be formed in the extension cap body. The extension cap body can include an opening in an open end of the body. The opening can be in communication with the hollow interior. The opening enables at least partial receipt of the pedicle screw extension into the hollow interior. The open end and an opposite end define an axial direction. An extension arm can extend outwardly from a side wall of the extension cap body substantially perpendicularly to the axial direction. The extension arm can include a proximal end closer to the extension cap body than an opposite distal end. A tulip can be attached to the distal end of the extension arm. The tulip is configured to receive a contouring rod. In another example, the extension arm can extend from a top of the extension cap body, or the end opposite of the opening for receipt of the pedicle screw extension.

A system is described for pedicle screw extension alignment in an orthopedic patient. The system includes multiple pedicle screw extensions. When aligned, these extensions can project a spine contour by extending from pedicle screws inserted into the spine. Alignment clamps are positionable on the pedicle screw extensions. The system includes a straightening rod with a length sufficient to extend between the pedicle screw extensions. The system can include at least one pair of straightening rods to force the pedicle screw extensions to be parallel, and in some examples can include several pairs of straightening rods overlapping from one extension to the next to make the extension rods parallel in at least two dimensions. The straightening rod(s) can be held in position by the alignment clamps. Placement of the alignment clamps over the pedicle screw extensions and insertion of the straightening rod(s) through the rod receptacles forces vertical alignment of the pedicle screw extensions, thus accurately projecting the spine contour.

DETAILED DESCRIPTION

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

In describing and claiming the present invention, the following terminology may be used in accordance with the definitions set forth below.

As used herein, "adjacent" refers to near or close sufficient to achieve a desired affect. Although direct physical contact is most common and preferred in the structures of the present technology, adjacent can broadly allow for spaced apart features which are near or close to one another.

As used herein, the term "substantially" refers to the complete or nearly complete extent or degree of an action, characteristic, property, state, structure, item, or result. The exact allowable degree of deviation from absolute completeness may in some cases depend on the specific context. However, generally speaking the nearness of completion will be so as to have the same overall result as if absolute and total completion were obtained.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Reference throughout this specification to "one embodiment", "an embodiment", or "a specific embodiment" means that a particular feature, structure, or characteristic described in connection with the embodiment is included in at least one embodiment of the present invention. Thus, the appearances of the phrases "in one embodiment", "in an embodiment", or "in a specific embodiment" in various places throughout this specification are not necessarily all referring to the same embodiment. Furthermore, the particular features, structures, or characteristics may be combined in any suitable manner in one or more embodiments.

Reference to directions, such as "up", "down", "side" etc., throughout this specification can be relative and are provided for reference and understanding purposes, and are not intended to be limiting to specification directions. Likewise, orientations, such as "vertical", "horizontal", and so forth are also not specifically limited to such orientations, but are provided for reference and understanding purposes only. Directions, orientations, and so forth can be varied from those described herein as will be understood by one skilled in the art. Furthermore, directions, orientations, and so forth are subject to differentiation by a position or orientation of an orthopedic patient.

Spinal fusion is a surgical technique used to combine two or more vertebrae. Spinal fusion is used primarily to eliminate pain caused by abnormal motion of the vertebrae by immobilizing the vertebrae themselves. Spinal fusion is most commonly performed in the lumbar region of the spine, but is also used to treat cervical and thoracic regions. Conditions where spinal fusion may be considered include degenerative disc disease, spinal disc herniation, discogenic pain, spinal tumors, vertebral fractures, scoliosis, kyphosis, spondylolisthesis, spondylosis, posterior rami syndrome, and other degenerative spinal conditions that cause instability of the spine.

In most cases, the fusion is augmented by a process called fixation, which often includes the placement of metallic pedicle screws (often made from titanium) to stabilize the vertebra to facilitate bone fusion. The fusion process typically takes 6-12 months after surgery. Some technologies are able to avoid fusion and preserve spinal motion. Minimally invasive techniques have also been introduced to reduce complications and recovery time for orthopedic patients undergoing surgery to correct spine abnormalities.

Figure 1:
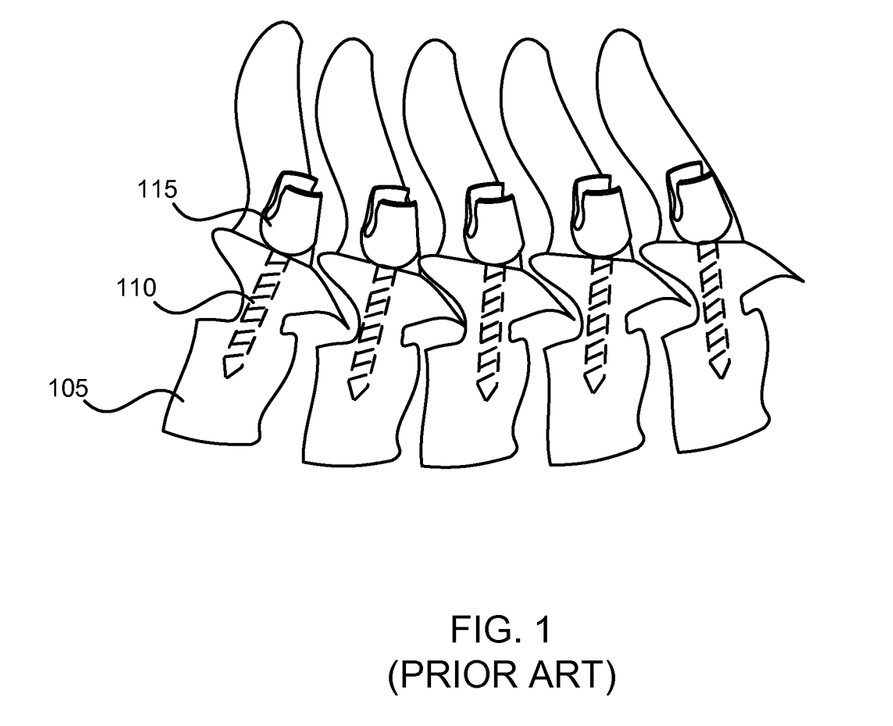
FIG. 1 is a side-view of a spinal column with pedicle screws inserted therein in accordance with prior art teachings.

Referring to FIG. 1, a partial side-view of a spinal column with pedicle screws 110 inserted therein is shown according to prior art teachings. The pedicle screws are inserted into pedicles on spinal vertebrae 105. A pedicle refers to the part of each side of a neural arch of a vertebra. Pedicle screws can be inserted into the pedicles on each side of each vertebra. However, for convenience and simplicity the accompanying figures illustrate a one-sided view of vertebrae in the spinal column and thus potentially half of the pedicle screws and other devices that may be inserted or otherwise involved in spinal fixation procedures. The pedicle screws can include, or have attached thereto, saddles or U-shaped channels, known as "tulips" 115. The tulips can be fixed or have a uni-axial or multi-axial rotation upon the head of the pedicle screw.

The channel in the tulip is configured to receive a contouring rod therein for maintaining or correcting a spinal curvature. Typically, a surgeon will perform at least one incision along the spinal column to insert the pedicle screws. The contouring rod is then placed in one or more tulips to determine where the contouring rod is to be bent or contoured to approximate the actual or desired curvature of the spine. The contouring rod may be repeatedly inserted, removed, and shaped until a desired contour is achieved. After the contouring rod is finally inserted into the tulips, caps can be attached to the tulips above the contouring rod to securely hold the contouring rod within the channel.

Figure 2:
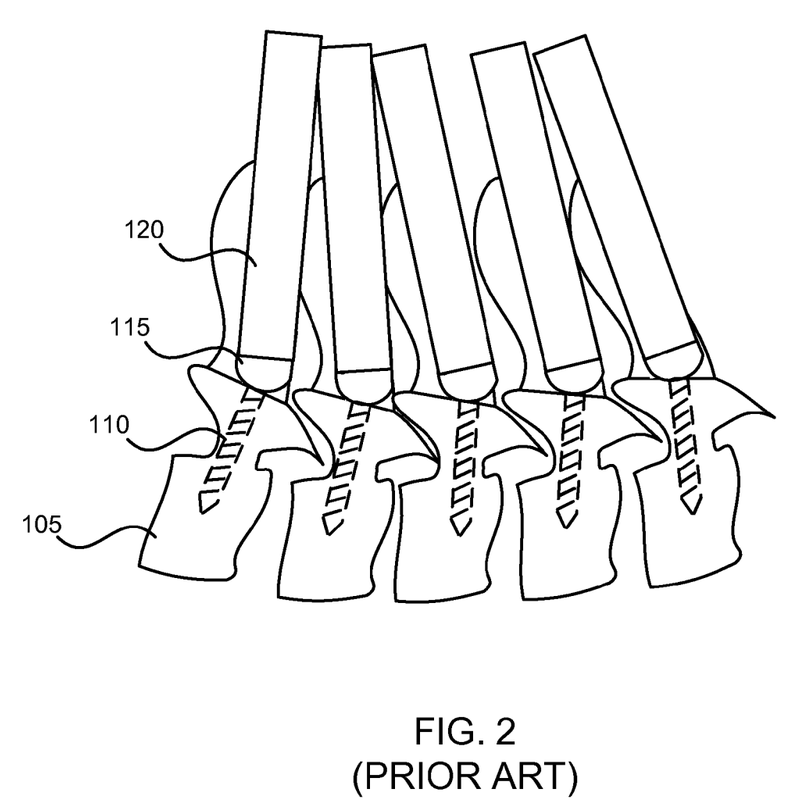
FIG. 2 is a side-view of a spinal column with pedicle screws inserted therein and pedicle screw extensions extending from the pedicle screws in accordance with prior art teachings.

Reference will now be made to FIG. 2. As described above, minimally invasive techniques have been introduced to reduce complications and recovery time for orthopedic patients undergoing surgery to correct spine abnormalities. One such technique involves the use of pedicle screw extensions. FIG. 2 is a partial side-view of a spinal column with pedicle screws 110 inserted into the vertebrae 105. Pedicle screw extensions 120 are attached to the tulips 115 on the pedicle screws. The extensions extend from the spinal column through the skin and other tissues adjacent the spinal column to an exterior of the patient. A tulip can be attached to the extension to allow a contouring rod to be bent or contoured outside of or removed from the patient's spine. The pedicle screws and extensions can be placed without the long incision along the spine as described in FIG. 1. The contouring rod, once shaped, can be inserted through an incision at one end of the surgical site and slid through each of the tulip channels.

While pedicle screw extensions are useful in minimizing the invasiveness of orthopedic surgical procedures, accurate shaping of contouring rods is further complicated because the pedicle screw extension positions are variable due to the rotatability of the tulips, upon which the pedicle screw extensions are situated. In FIG. 1, though the tulips may be rotatable, the position and height of the vertebrae are not.

Figure 3:
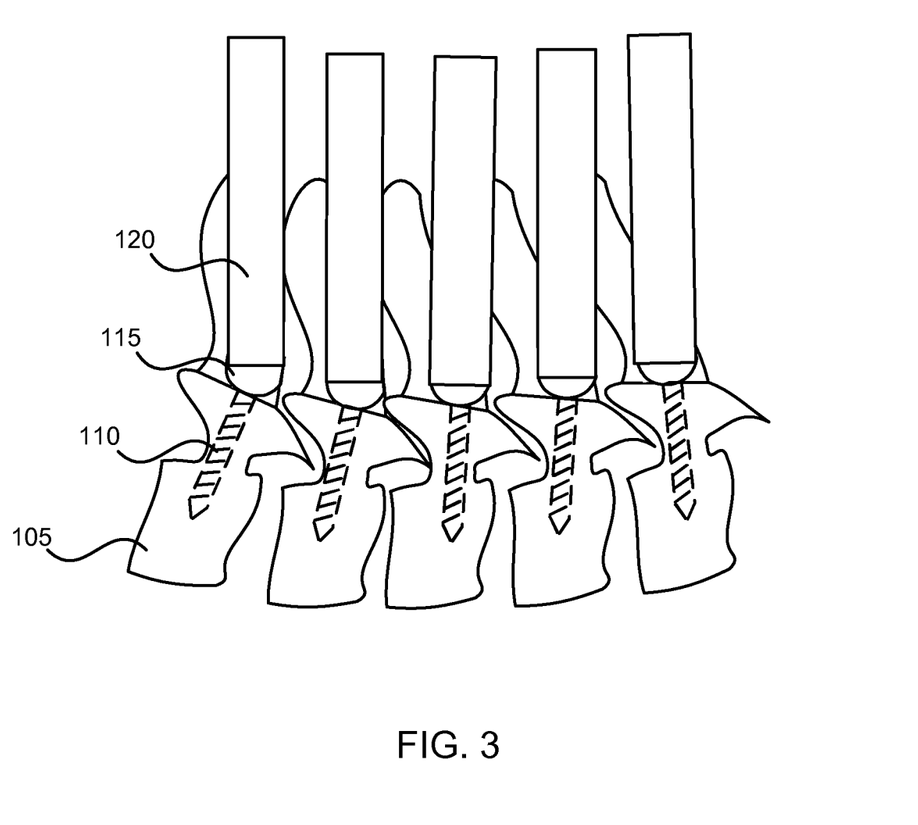
FIG. 3 is a side-view of a spinal column with pedicle screws inserted therein and vertically aligned pedicle screw extensions extending therefrom according to an embodiment.

Referring to FIG. 3, the present technology uses vertical alignment of the pedicle screw extensions to provide a substantially accurate projection of a spinal contour along a top of the pedicle screw extensions. Maintenance of the projected contour by maintaining the vertical alignment of the extensions can reduce inaccuracies and mistakes in shaping the contouring rod as well as reduce time expenditure (and cost) in shaping the contouring rod. The systems and methods described herein can be used in spinal fusion and other surgical fixation techniques.

Figure 4A:
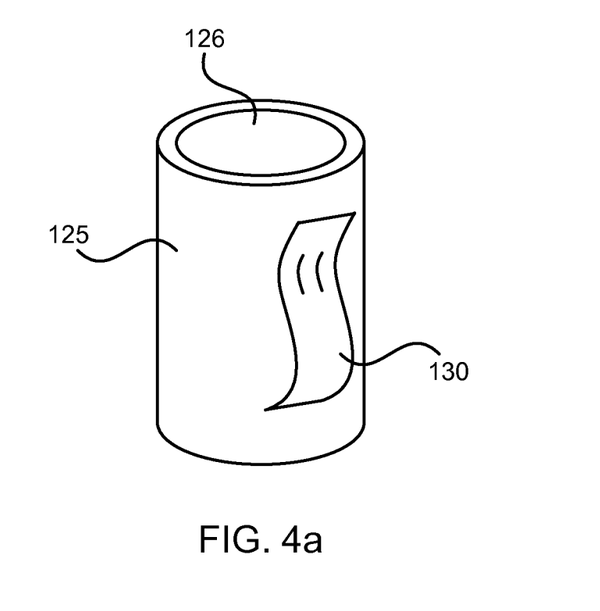
FIG. 4a is a perspective view of an alignment clamp for alignment of pedicle screw extensions in accordance with an embodiment.
Figure 4B:
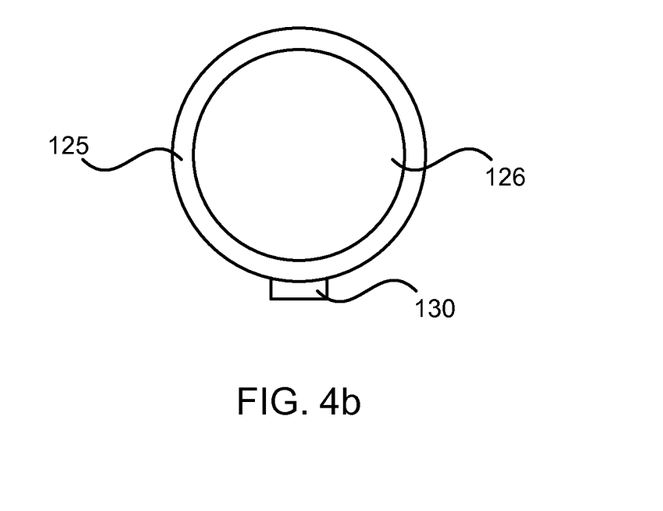
FIG. 4b is a top view of an alignment clamp for alignment of pedicle screw extensions in accordance with an embodiment.

Referring to FIGS. 4a-4b, an alignment clamp 125 for alignment of pedicle screw extensions is shown in accordance with an embodiment. The alignment clamp can have a hollow interior 126. The clamp can be configured to receive a pedicle screw extension through the hollow interior. The clamp includes opposing open ends in communication with the hollow interior. The pedicle screw extension can be inserted into the alignment clamp, or rather the clamp can be positioned over the pedicle screw extension, via the open ends. The alignment clamp can be formed from any suitable material, such as plastic, rubber, metal, and the like. The hollow interior of the alignment clamp can be formed to have a marginally larger diameter than a diameter of the pedicle screw extension. In accordance with embodiments, the alignment clamp can have a diameter sufficiently narrow that the alignment clamp fits snugly over the pedicle screw extension such that the alignment clamp does not slide freely on the extension but is movable upon application of force. The snug fit of the alignment clamp enables use of existing extensions and an easier to position alignment clamp. According to other embodiments, spring-loaded pins, adhesives, or other devices for fixing the alignment clamp in a desired position on the pedicle screw extension may also be used.

Figure 5:
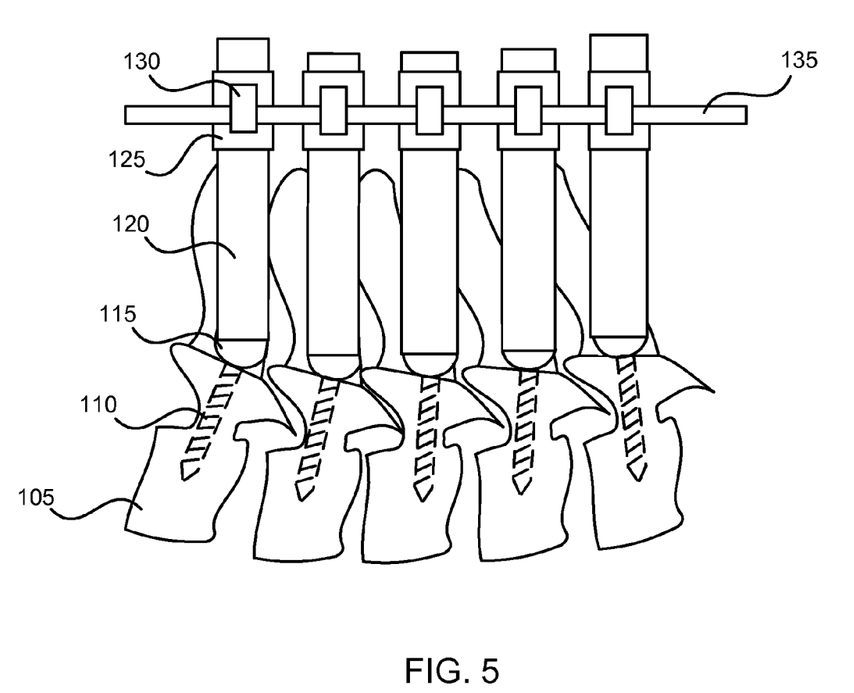
FIG. 5 is a side-view of a spinal column with pedicle screw extensions in alignment using an alignment clamp and a straightening rod in accordance with an embodiment.

The alignment clamp 125 can include a straightening rod receptacle 130 on a side of the clamp. Referring to FIG. 5, the straightening rod receptacle can be oriented to receive a straightening rod 135 therethrough. The straightening rod can comprise a straight rod. Typically the straightening rod can be formed from metal, such as steel, titanium, or any other suitable metal. The straightening rod can be received by the straightening rod receptacles of multiple alignment clamps positioned on multiple pedicle screw extensions 120. In order for the straightening rod to be received by the straightening rod receptacles, one or more of the alignment clamps may be adjusted upward or downward along a length of the pedicle screw extensions with respect to one another to accommodate the straightness of the straightening rod.

The straightening rod receptacles can be configured to receive the straightening rod at a precise angle. For example, the straightening rod receptacle can be oriented substantially perpendicular to a direction of the clamp through which the pedicle screw extension is receivable. In other words, when both a straightening rod and a pedicle screw extension are received by the alignment clamp, the straightening rod and the pedicle screw extension can be substantially perpendicular to one another. Because each of the alignment clamps can be configured to maintain the perpendicular orientation of the straightening rod and the pedicle screw extension with respect to one another, each of the pedicle screw extensions are forced into a vertical alignment with respect to one another. As can be appreciated from FIG. 5, the vertical alignment of the pedicle screw extensions causes a projection of the contour of the spine along the tops of the pedicle screw extensions.

The straightening rod receptacle can be configured as a passive mechanical receptacle or alternatively as an active mechanical receptacle. For example, a passive mechanical receptacle may comprise a circular hole, a u-shaped saddle, a clip, or any other passive mechanical structure capable of holding the straightening rod. In one aspect, the straightening rod receptacle may comprise a diameter marginally larger than a diameter of the straightening rod such that the straightening rod fits snugly within the straightening rod receptacle. Active mechanical straightening rod receptacles may likewise provide a snug fit of the straightening rod. Examples of active mechanical straightening rod receptacles include a spring-loaded clip, a spring-loaded pin (or pin-receptacle for receiving a spring-loaded pin on the straightening rod), a clamp, or any other active mechanical structure capable of holding the straightening rod. Whether active mechanical or passive mechanical, the straightening rod receptacle may be formed from a same material or a different material than the alignment clamp on which it is formed. For example, the alignment clamp may be formed from a plastic or polymer and the straightening rod receptacle may be formed from a metal.

Figure 6A:
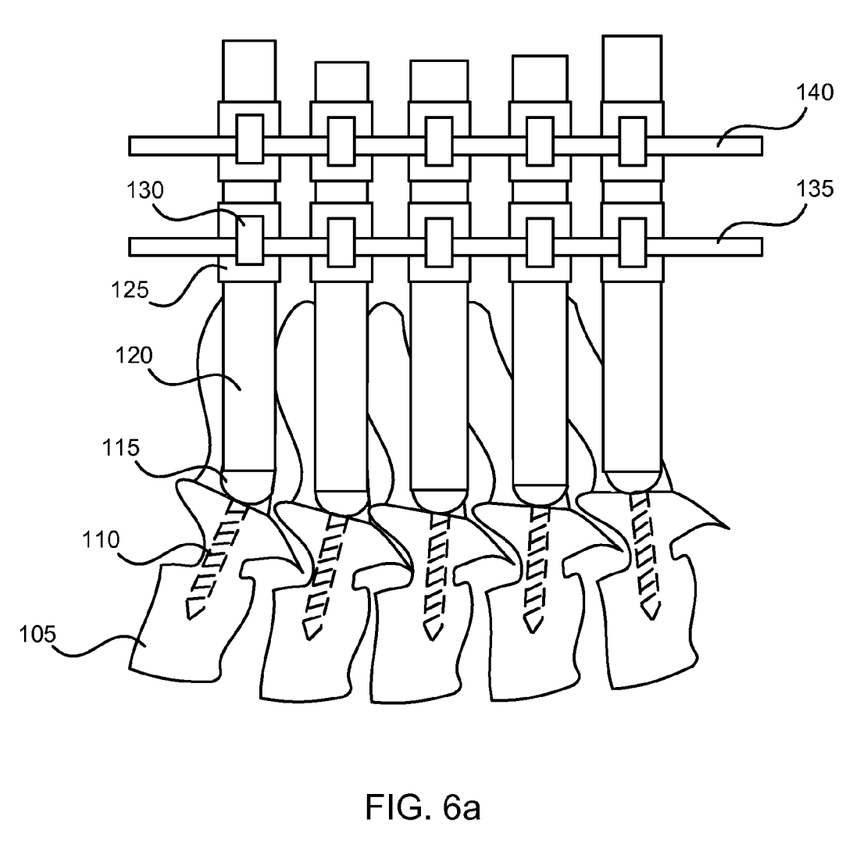
FIG. 6a is a side-view of a spinal column with pedicle screw extensions in alignment using multiple alignment clamps and straightening rods to maintain an axial alignment with the spinal column in accordance with an embodiment.

Referring to FIG. 6a, according to some embodiments, multiple straightening rods 135, 140 may be used for alignment of the pedicle screw extensions 120. For example, multiple alignment clamps 125 may be positioned on each of the pedicle screw extensions. In one aspect, the alignment clamps may be positioned substantially adjacent to one another. In another aspect, the alignment clamps may be positioned with a space therebetween. While use of a single straightening rod is useful for vertically aligning the pedicle screw extensions, use of multiple straightening rods can prevent lateral misalignment of the straightening rods (e.g., twisting). For example, though a single straightening rod may be capable of vertically aligning the pedicle screw extensions, the pedicle screw extensions can still be rotated upon the tulips 115 and become misaligned laterally with the actual spine.

Figure 6B:
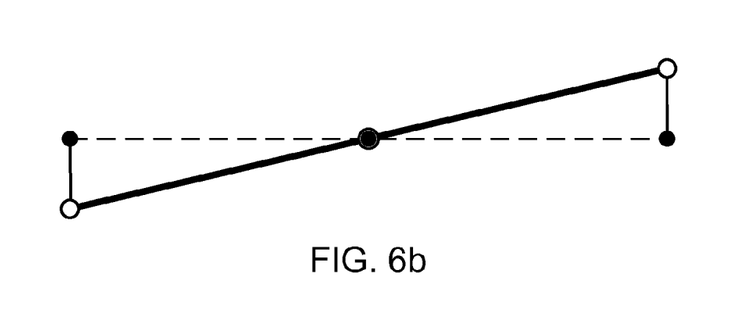
FIG. 6b is a top schematic view of laterally misaligned pedicle screw extensions with a single straightening rod.

For example, referring to FIG. 6b, the dotted line can represent the spine. The black circles can represent where the pedicle screws are attached to the spine. The white circles can represent a position of a distal end of the pedicle screw extensions from the spine. The thin black lines extending between the black and white circles at the right and left ends of the figure can represent the pedicle screw extensions. The thick black line can represent the straightening rod. Thus, as can be appreciated, though the alignment clamps are in position to hold the straightening rod, misalignment of the contouring rod to be shaped upon the tops of the pedicle screw extensions can occur if the pedicle screw extensions are not maintained in a proper position with respect to one another and/or the spine. Use of a second straightening rod 140 can force lateral alignment of the pedicle screw extensions and prevent a skewed result as in FIG. 6b.

Figure 7:
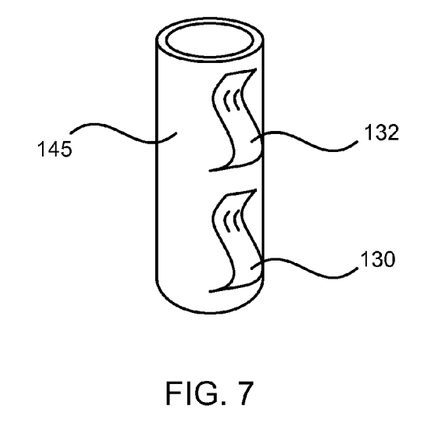
FIG. 7 is perspective view of an alignment clamp configured to receive multiple straightening rods in accordance with an embodiment.

Referring to FIG. 7, an alignment clamp is shown which is similar in many regards to the alignment clamp shown in FIG. 4a and described above. For example, the alignment clamp can include a body 145, a hollow interior, and a straightening rod receptacle 130. The alignment clamp of FIG. 7 differs from FIG. 4a in that the alignment clamp of FIG. 7 features an additional, or second, straightening rod receptacle 132. The second straightening rod receptacle can be configured just as the first. The second straightening rod can be oriented similarly as the first straightening rod receptacle such that the first and second straightening rod receptacles can retain a plurality of straightening rods substantially parallel to one another. Furthermore, the plurality of straightening rods can be held substantially perpendicular to pedicle screw extension which may extend through the hollow interior of the alignment clamp body. Inclusion of multiple straightening rod receptacles on a single alignment clamp can simplify a process and reduce a configuration time of positioning and installing alignment clamps and straightening rods, particularly when multiple straightening rods are used.

A combination of dual straightening rod receptacle alignment clamps and single straightening rod receptacle alignment clamps may also be used. For example, a dual straightening rod receptacle alignment clamp may be positioned on a pedicle screw extension and multiple single straightening rod receptacle alignment clamps may be positioned on a neighboring pedicle screw extension.

Figure 8:
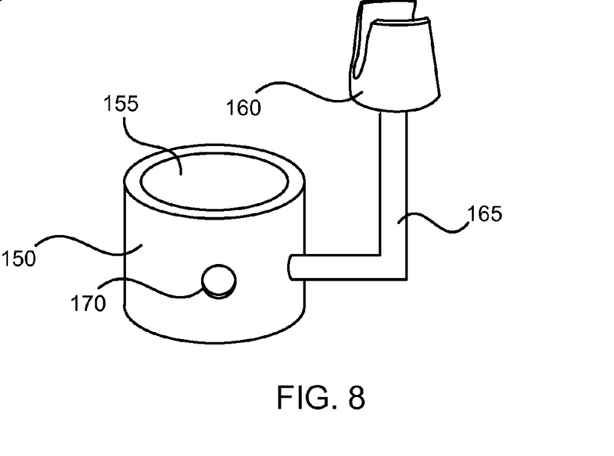
FIGS. 8-9 are perspective views of extension caps for a pedicle screw extensions in accordance with embodiments.

Referring to FIG. 8, an extension cap for a pedicle screw extensions is shown in accordance with embodiments. As described above, a tulip can be positioned or attached to the tops of the pedicle screw extensions to facilitate shaping of the contouring rod along the tops of the pedicle screw extensions. The extension cap can be positioned on a pedicle screw extension at or near the distal end of the pedicle screw extension from the patient's spine. The extension cap can be removably attachable to the pedicle screw extension and thus result in a removably attachable tulip (from the pedicle screw extension) for receiving the contouring rod.

The extension cap can include an extension cap body 150. A hollow interior can be formed in the extension cap body. The exterior of the extension cap body and the hollow interior can be cylindrically shaped. Other shapes are also considered within the scope of this disclosure. However, since pedicle screw extensions are primarily cylindrically shaped, a corresponding shape for the extension cap body and/or hollow interior can be used in some embodiments. The extension cap body comprises at least one opening 155 in an open end of the extension cap body which is in communication with the hollow interior. The opening enables at least partial receipt of the pedicle screw extension into the hollow interior. For example, one end of the extension cap body may comprise a closed end. In this example, the pedicle screw extension is not fully insertable through the extension cap body. However, in another example, the extension cap body comprises two open ends, opposite one another. Opposing open ends can enable passage of the pedicle screw extension through the extension cap to any desired extent. A motivation for allowing complete passage of the pedicle screw extension through the extension cap body is described below.

Whether the extension cap body 150 comprises one or multiple open ends, the open end and an opposite end can define an axial direction of the extension cap, or an axial direction of the extension cap body. An extension arm 165 can extend outwardly from a side wall of the extension cap body substantially perpendicularly to the axial direction. The extension arm can include a proximal end close to the extension cap body and an opposite distal end farther from the extension cap body than the proximal end. A tulip 160 can be attached to the distal end of the extension arm and be configured to receive a contouring rod therein. In one aspect, the extension cap body can include a slot to receive a protrusion on a pedicle screw extension to prevent the extension cap body from twisting on the pedicle screw extension. In another aspect, the extension cap body can include a protrusion configured to be received by a slot on the pedicle screw extension to prevent twisting.

A combination of an extension cap comprising two opposing open ends with an extension arm extending from the side wall of the extension cap body can enable detachment of a tulip, extension cap, pedicle screw extension, alignment clamp, and/or pedicle screw when a contouring rod is in position on other neighboring tulips. For example, if at some point during the surgery, a problem is recognized with a piece of hardware (such as a tulip, extension cap, pedicle screw extension, alignment clamp, and/or pedicle screw, etc.) or there arises an issue of placement or alignment of the piece of hardware, removal of a contouring rod to remedy the issue or problem can be time consuming and possibly result in malformation of the contouring rod during the removal and reinstallation process. However, with an extension cap with two opposing open ends, the extension cap can be moved down along a length of the pedicle screw extension away from the distal end of the rod and the tulip can be removed from the contouring rod. Because the pedicle screw extension is rotatable upon the tulip under the skin the pedicle screw extension can be rotated away from alignment with the other pedicle screw extensions. The straightening rod receptacle in this example can be configured to allow release of the straightening rod when the pedicle screw extension is rotated away. Thus, the positioning and alignment of a single pedicle screw extension is affected while the positioning and alignment of all of the other pedicle screw extensions, straightening rods, contouring rods, and so forth can remain.

Referring still to FIG. 8, the extension arm 165 extending from the side of the extension cap body 150 can comprise a vertical section and a horizontal section. A 90° elbow can be provided at the intersection of the vertical and horizontal sections. The tulip 160 can be positioned at the top of the vertical section at an end opposite the intersection with the horizontal section. In other words, the tulip can be positioned substantially perpendicularly to the extension arm (or at least the horizontal section of the extension arm) and parallel to the axial direction. Regarding the tulip orientation for parallel alignment with the axial direction, an attachment end of the tulip for attaching to a pedicle screw, extension cap, or the like, and an opposing end for receiving the contouring rod within the channel may comprise a tulip axial direction. The tulip axial direction can be parallel to the extension cap body axial direction. By including the elbow in the extension arm, the tulip can be facing upwards so that when the extension cap is slid downwards on the pedicle screw extension the tulip can freely slide down and away from the contouring rod when held in position by neighboring tulips.

The extension cap can further comprise an attachment device. The attachment device can be configured to attach the extension cap to the pedicle screw extension. In one aspect, the extension cap can comprise a snug fit, similar to the alignment clamps described above. However, physically attaching the extension cap to the pedicle screw extension can prevent unintentional displacement of the extension cap along the length of the pedicle screw extension. (In a snug fit configuration, application of a force is sufficient to displace the extension cap, which in turn can cause inaccurate shaping of the contouring rod). Though a couple of examples of attachment devices are described below, the examples are non-exhaustive and intended to be non-limiting. Indeed, the attachment device may comprise any suitable device or mechanism for fixing the position of the extension cap with respect to the pedicle screw extension.

In one example, the attachment device may comprise screw threads within the hollow interior of the extension cap body. Mating screw threads can be formed on the end of the pedicle screw extension. In one aspect, the mating screw threads can extend only partially along the pedicle screw extension to provide a stopping point for the extension cap.

In another example, the pedicle screw extension comprises an end with a narrower end section than a main section of the pedicle screw extension. The attachment device of the extension cap in this example comprises a hollow interior with a diameter wide enough to receive the narrower end section but not the main section, and bottom portion of the extension cap body configured to abut a flange connecting the narrow and main sections of the pedicle screw extension. In another aspect, the end section and the hollow interior may comprise a different shape than the main section and not necessarily comprise a different diameter. For example, the main section may comprise a circular cross-shape, while the end section and hollow interior can have a different cross-shape, such as a square, a star, etc. Including a shape with a different cross section can eliminate the need for a different diameter and can also serve to firmly maintain an angular rotation of the extension cap upon the pedicle screw extension.

In another example, the attachment device comprises a spring-loaded pin extending from an inner sidewall of the extension cap into the hollow interior. The spring-loaded pin can extend into a pedicle screw extension hole when the extension cap is positioned on the pedicle screw extension. The spring-loaded pin can serve to maintain a vertical position and an angular rotation of the extension cap on the pedicle screw extension. The spring-loaded pin is depressable when the contouring rod is received by a plurality of tulips on a plurality of pedicle screw extensions to enable adjustment of an individual pedicle screw extension without removing the contouring rod from all of the plurality of tulips or without affecting all of the plurality of pedicle screw extensions, as has been described above. In another example, as shown in FIG. 8, the extension cap comprises a hole 170 for receiving a spring-loaded pin on a pedicle screw extension. The hole can extends from the hollow interior at least partially through the side wall of the extension cap body. For example, a hole extending completely through the side wall can enable protrusion of the spring-loaded pin to the outside of the extension cap such that a user can press against the spring-loaded pin to release the extension cap. In another example, the hole comprises a depression that extends only partially within the side wall and the spring-loaded pin comprises rounded edges such that application of a force along the axial direction can cause depression of the spring-loaded pin to release the extension cap.

Figure 9:
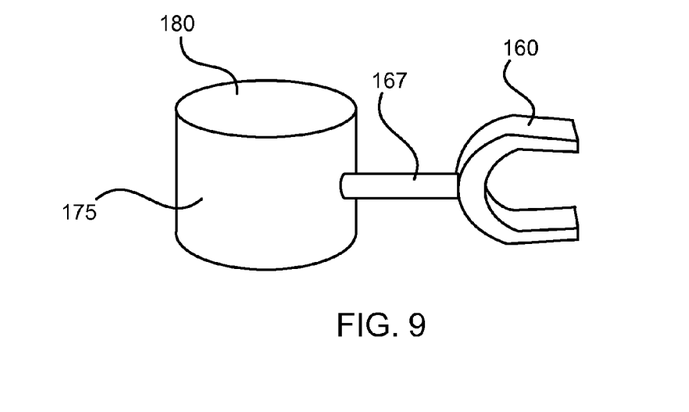

Referring to FIG. 9, an extension cap is shown which includes an extension cap body 175 having a hollow interior, an open end, and a closed end 180. In this example, the closed end can serve as the attachment device described above to fix the position of the extension cap on the pedicle screw extension. A straight extension arm 167 extends from a side wall of the extension cap body, perpendicularly to the axial direction of the extension cap body. A tulip 160 is attached at the distal end of the extension arm. The tulip can be a fixed, uni-axial, or multi-axial tulip. The perpendicular extension arm can serve multiple purposes. For example, if an issue or problem arises with the pedicle screw extension, or an alignment clamp, pedicle screw, etc. associated the pedicle screw extension to which the extension cap is attached, the pedicle screw extension can be rotated away from the straightening rod and/or contouring rod without detaching the extension cap, as in the examples described above regarding FIG. 8. In an example where the straightening rod is not laterally removable from the straightening rod receptacle on the alignment clamp, the straightening rod can be removed prior to the rotation of the pedicle screw extension away from alignment with other pedicle screw extensions, without affecting a contouring rod. Also, as will be described below, extensions at different spine segments may be at different heights due to spine curvature and including connecting devices for connecting the extensions. To prevent potential interference with the contouring rod from the connecting devices, an extension arm extending to the side of the extension cap can enable shaping of the contouring rod away from the potential interference.

In other examples not shown, the extension cap may comprise a tulip positioned on the top of the extension cap body, or positioned over the closed end of the extension cap body. The extension cap in this example may or may not include an extension arm between the extension cap body and the tulip. In yet other examples, the extension arm is configured as a flexible, detachable, and/or frangible extension arm to enable adjustment of an individual pedicle screw extension, pedicle screw, etc. as described above without disrupting alignment of other pedicle screw extensions, positioning of straightening or contouring rods, etc.

Figure 10:
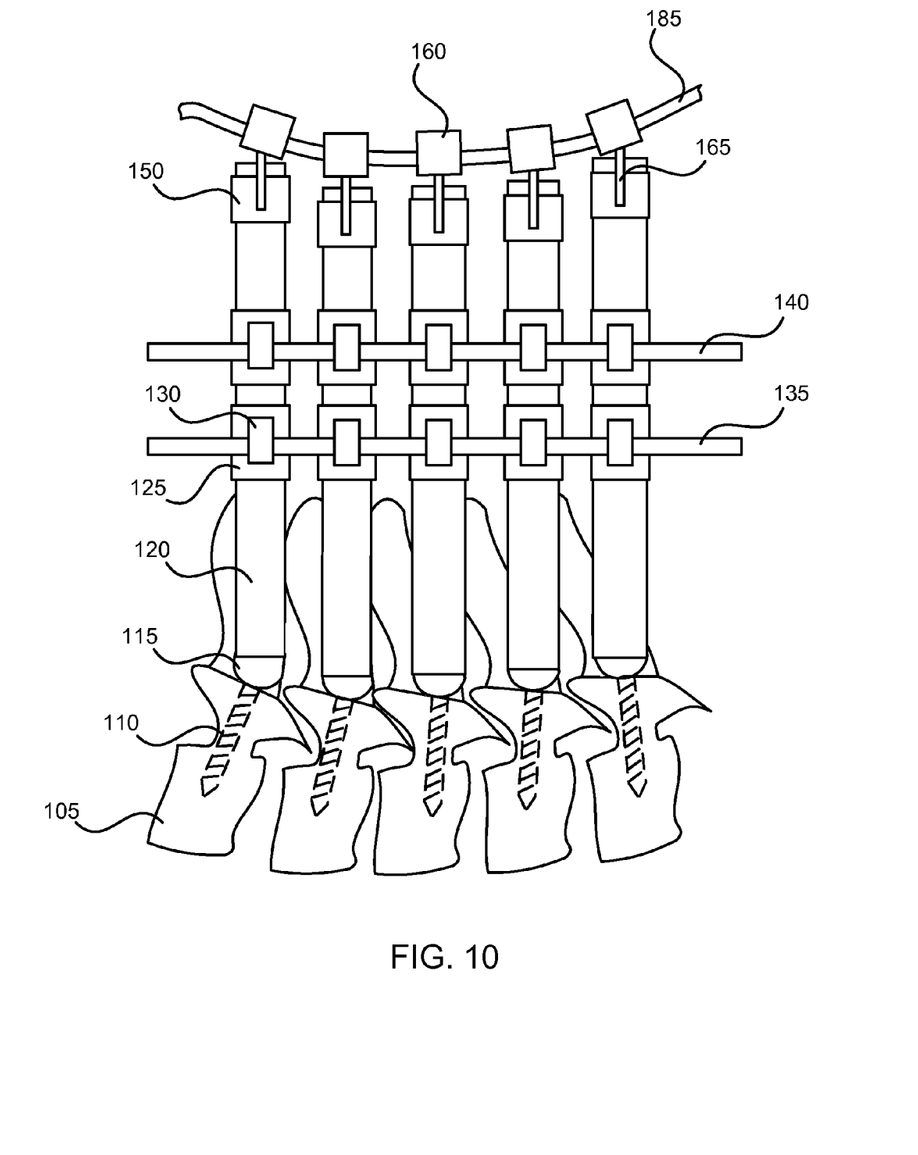
FIG. 10 is a side-view of a spinal column with pedicle screw extensions, alignment clamps, straightening rods, and extension caps in accordance with an embodiment.

Referring to FIG. 10, a system for pedicle screw extension alignment in an orthopedic patient is shown which includes the components described above. The various components together enable vertical and lateral alignment of pedicle screw extensions and individual adjustability of the components even when straightening rods or contouring rods are in position in the alignment clamps or tulips. Specifically, a plurality of pedicle screw extensions 120 are attached to tulips 115 on pedicle screws 110 inserted into vertebrae 105. The pedicle screw extensions are configured to project a spine contour by vertical alignment one with another. A plurality of alignment clamps 125 are positionable on the plurality of pedicle screw extensions. One or more straightening rods 135, 140 can extend between the plurality of pedicle screw extensions and be held in position by receptacles 130 on the plurality of alignment clamps to force vertical alignment of the plurality of pedicle screw extensions. Extension caps 150 can be attached to the pedicle screw extensions at a predetermined position to accurately maintain the projection of the spine contour and include an extension arm 165 extending to tulips 160 configured for receiving a contouring rod 185.

A curved spine may comprise a significant or abnormal curvature due to severe lordosis or kyphosis, for example. The curvature may be sufficient to prevent use of a single straightening rod along the spine. For spines exhibiting severe or abnormal curvature that would prevent use of a single straightening rod, multiple straightening rods can be used along different spine segments. Use of multiple straightening rods along different spine segments allows for alignment of the pedicle screw extensions at each segment. However, each segment may not necessarily be in alignment with another segment. A connection device can thus be used between the segments to force alignment of different segment with one another.

As described above, the pedicle screw extensions can be aligned in a substantially vertical orientation. The straightening rods can be substantially perpendicular to the pedicle screw extensions in a substantially horizontal orientation. Straightening rod connectors can be used to maintain a constant alignment across the different segments or regions of the curved spine. The straightening rod connectors can be used in connection with a vertical rod or vertical straightening rod segment. The straightening rod connectors can be configured to receive one or more straightening rods in a first receptacle and one or more vertical rods in a second receptacle. In one aspect, the straightening rod connectors can be configured to provide a snug fit, as has described above regarding the alignment clamps. In one aspect, the straightening rod connectors can be configured to hold the straightening and vertical rods substantially perpendicular to one another. Other angled orientations are also considered. The straightening rod connectors can be configured to maintain a lateral alignment of pedicle screw extensions along differing spine segments. Further, the straightening rod connectors can enable vertical alignment of pedicle screw extensions along one spine segment with those of another spine segment.

Figure 11:
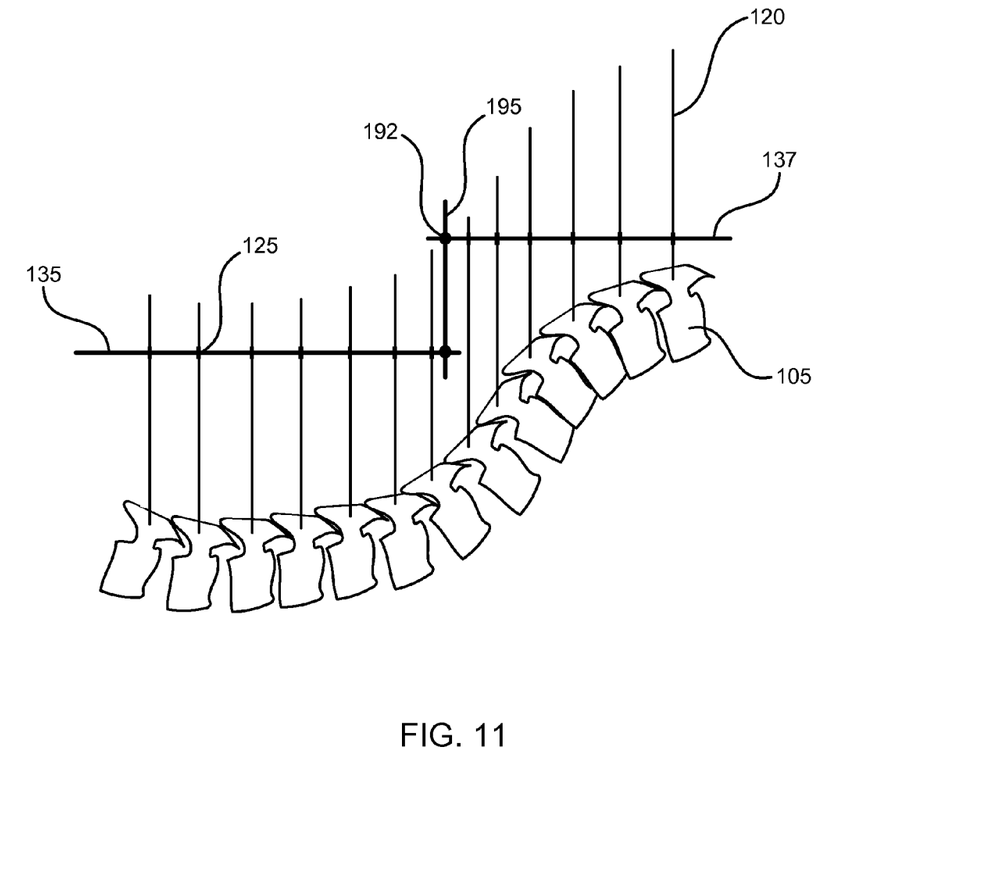
FIG 11 is a side-view of a spinal column, wherein multiple straightening rods are connected to maintain alignment along the curved spine in accordance with an embodiment.

Referring to FIG. 11, a partial side-view of a spinal column 105 is shown, wherein a system of straightening rods 135, 137 and alignment clamps 125 are used to align pedicle screw extensions 120 at different positions or segments along a curved spine, and multiple straightening rods are connected using straightening rod connectors 192 and a vertical rod segment 195. The vertical rod segment is attachable at a first end to a first straightening rod (using a straightening rod connector) for a first segment of the spine contour, and the vertical rod segment is further attachable at a second end to a second straightening rod (using a straightening rod connector) for a second segment of the spine contour. As will be appreciated, due to the length of the pedicle screw extensions and the curvature of the spine, a single straightening rod is unable to be attached across all of the pedicle screw extensions, and thus, the straightening rod connection device (including the connectors and vertical rod) enables use of the alignment systems along even severely curved spines.

Figure 12A:
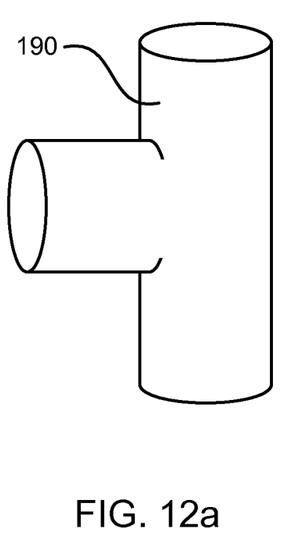
FIGS. 12a-12c are perspective views of straightening rod connectors for connecting multiple straightening rods in accordance with an embodiment.
Figure 12B:
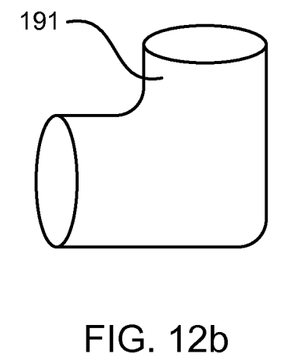
Figure 12C:
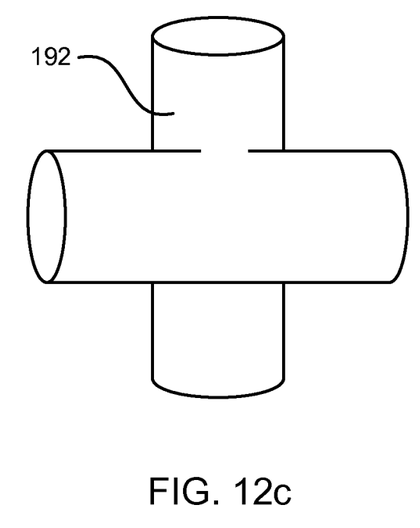

Referring to FIGS. 12a-12c, straightening rod connectors 190, 191, 192 are shown for connecting multiple straightening rods at different positions along a substantially curved spine in accordance with an embodiment. The straightening rod connectors may comprise any suitable shape or material and may comprise any suitable configuration for receiving and holding the straightening rods and vertical rods, as can be readily understood from FIGS. 12a-12c. Also, though not shown, the connectors can include receptacles for multiple straightening rods and/or multiple vertical rods. Alternatively, in configurations where multiple straightening and/or vertical rods are employed, multiple straightening rod connectors may be used. Use of multiple straightening and/or vertical rods can enable more precise vertical and/or lateral alignment of pedicle screw extensions along different spine segments.

The described features, structures, or characteristics herein may be combined in any suitable manner in one or more embodiments. In the preceding description, numerous specific details were provided, such as examples of various configurations to provide a thorough understanding of embodiments of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A system for percutaneous pedicle screw extension alignment in an orthopedic patient, comprising:
   a plurality of percutaneous pedicle screw extensions configured to project a spine contour by extending from a plurality of pedicle screws;
   a plurality of alignment clamps positionable on the plurality of percutaneous pedicle screw extensions;
   a straightening rod comprising a length sufficient to extend between the plurality of percutaneous pedicle screw extensions and to be held in position by the plurality of alignment clamps; and
   an extension cap for the plurality of percutaneous pedicle screw extensions, the extension cap comprising:
      an extension cap body;
      a hollow interior formed in the extension cap body;
      an opening in an open end of the extension cap body and in communication with the hollow interior, wherein the opening enables at least partial receipt of the pedicle screw extension into the hollow interior;
      a tulip attached to the extension cap body and configured to receive a contouring rod therein; and
      an extension arm extending outwardly from a side wall of the extension cap body, the extension arm comprising a proximal end closer to the extension cap body than an opposite distal end;
   wherein placement of the plurality of alignment clamps over the plurality of percutaneous pedicle screw extensions and insertion of the straightening rod through the rod receptacles provides parallel vertical alignment of the plurality of percutaneous pedicle screw extensions.

2. A system in accordance with claim 1, wherein the straightening rod comprises a plurality of discrete straightening rods, and wherein placement of the plurality of alignment clamps over the plurality of percutaneous pedicle screw extensions and insertion of the plurality of discrete straightening rods through the rod receptacles provides vertical alignment of the plurality of percutaneous pedicle screw extensions and axial alignment of the plurality of discrete straightening rods with the plurality of pedicle screws.

3. A system in accordance with claim 1, wherein the plurality of alignment clamps comprises:
a plurality of alignment clamps having hollow interiors and configured to receive the plurality of pedicle screw extensions therethrough, the plurality of alignment clamps comprising opposing open ends in communication with the hollow interior; and
a plurality of straightening receptacles on sides of the plurality of alignment clamps and oriented to receive a straightening rod through the plurality of straightening rod receptacles, the plurality of straightening rod receptacles being substantially perpendicular to a direction of the plurality of alignment clamps through which the plurality of pedicle screw extensions are receivable.

4. A system in accordance with claim 3, wherein the plurality of straightening rod receptacles comprises multiple similarly oriented straightening rod receptacles on the side of each of the plurality of alignment clamps.

5. A system in accordance with claim 1, further comprising a vertical segment perpendicular to the straightening rod and substantially perpendicular to the spine contour, the vertical segment being attachable to a plurality of straightening rods positioned along different segments of the spine contour to enable pedicle screw extension alignment using straightening rods on spines exhibiting severe lordosis or kyphosis.

6. A system in accordance with claim 5, wherein the plurality of straightening rods comprises at least two straightening rods at a first segment of the spine contour and at least two straightening rods at a second segment of the spine contour, wherein the vertical segment is attachable at a first end to the at least two straightening rods for the first segment of the spine contour and the vertical segment is attachable at a second end to the at least two straightening rods for the second segment of the spine contour.

7. A system in accordance with claim 1, wherein the tulip is positioned perpendicularly to the extension arm and parallel to the axial direction.

8. A system in accordance with claim 1, wherein the tulip is positioned parallel to the extension arm and perpendicularly to the axial direction.

9. A system in accordance with claim 1, wherein the tulip comprises a multi-axial tulip.

10. A system in accordance with claim 1, further comprising an attachment device configured to attach the extension cap to the percutaneous pedicle screw extension.

11. A system in accordance with claim 1, further comprising a contouring rod configured to extend between the plurality of percutaneous pedicle screw extensions and which is deformable to represent the projected contour of the spine.

12. A method for using the system according to claim 1, wherein the straightening rod comprises a plurality of straightening rods, the method comprising:
positioning at least two of the plurality of alignment clamps on each of the plurality of percutaneous pedicle screw extensions at different vertical positions along a length of an individual of the percutaneous pedicle screw extensions; and
affixing the plurality of straightening rods between the plurality of percutaneous pedicle screw extensions using the at least two of the plurality of alignment clamps on each of the plurality of percutaneous pedicle screw extensions such that an individual of the plurality of alignment clamps receives an individual of the plurality of straightening rods and the individual of the plurality of straightening rods is received by a multiple of the plurality of alignment clamps;
wherein the plurality of straightening rods are aligned, parallel and arranged in a vertically stacked configuration when viewed from a side of a plane defined by an axial direction of the plurality of percutaneous pedicle screw extensions and a linear direction between the plurality of percutaneous pedicle screw extensions.

13. A system for percutaneous pedicle screw extension alignment in an orthopedic patient, comprising:
a plurality of percutaneous pedicle screw extensions configured to project a spine contour by extending from a plurality of pedicle screws;
a plurality of alignment clamps positionable on the plurality of percutaneous pedicle screw extensions;
a straightening rod comprising a length sufficient to extend between the plurality of percutaneous pedicle screw extensions and to be held in position by the plurality of alignment clamps; and
an extension cap for the plurality of percutaneous pedicle screw extensions, the extension cap comprising:
an extension cap body;
a hollow interior formed in the extension cap body;
an opening in an open end of the extension cap body and in communication with the hollow interior, wherein the opening enables at least partial receipt of the pedicle screw extension into the hollow interior; and
a multi-axial tulip attached to the extension cap body and configured to receive a contouring rod therein;
wherein placement of the plurality of alignment clamps over the plurality of percutaneous pedicle screw extensions and insertion of the straightening rod through the rod receptacles provides parallel vertical alignment of the plurality of percutaneous pedicle screw extensions.

* * * * *